(12) United States Patent
Kalfas et al.

(10) Patent No.: US 9,918,748 B2
(45) Date of Patent: Mar. 20, 2018

(54) SPINAL ROD CONNECTOR

(71) Applicant: DePuy Spine Sarl, Le Iocle (CH)

(72) Inventors: Iain Kalfas, Beachwood, OH (US);
Tom Doherty, Bellingham, MA (US);
David Selvitelli, Millis, MA (US);
Stephen Johnson, Johnston, RI (US);
Michael Mazzuca, North Easton, MA (US)

(73) Assignee: DEPUY SPINE SARL, Chemin Blanc 36, Le Locle (CH)

( * ) Notice: Subject to any disclaimer, the term of this patent is extended or adjusted under 35 U.S.C. 154(b) by 94 days.

(21) Appl. No.: 14/628,709

(22) Filed: Feb. 23, 2015

(65) Prior Publication Data

US 2015/0164555 A1 Jun. 18, 2015

Related U.S. Application Data

(63) Continuation of application No. 14/334,994, filed on Jul. 18, 2014, now Pat. No. 8,998,957, which is a
(Continued)

(51) Int. Cl.
*A61B 17/70* (2006.01)
(52) U.S. Cl.
CPC ........ *A61B 17/705* (2013.01); *A61B 17/7049* (2013.01)
(58) Field of Classification Search
CPC .............. A61B 17/7049; A61B 17/705; A61B 17/7023
(Continued)

(56) References Cited

U.S. PATENT DOCUMENTS

| 4,114,846 A | 9/1978 | Petersen |
| 4,920,959 A * | 5/1990 | Witzel ................. A61B 17/645 606/53 |

(Continued)

FOREIGN PATENT DOCUMENTS

| EP | 0737448 A1 | 10/1996 |
| EP | 1312316 A2 | 5/2003 |

(Continued)

OTHER PUBLICATIONS

European Search Report for Application No. 09178430.6, 10 pages, dated Feb. 22, 2010.
(Continued)

*Primary Examiner* — Pedro Philogene
*Assistant Examiner* — David C Comstock
(74) *Attorney, Agent, or Firm* — Raymond N. Scott, Jr.

(57) ABSTRACT

A rod connector for joining a first rod and a second rod includes bore holes that are offset and/or non-parallel to each other. The rod connector provides an offset or non-parallel connection between the rods that allows for the rods to match the contour of a patient's body without requiring bending of the rods. The rod connector may include a first bore hole for receiving the first spinal rod and a second bore hole for receiving the second spinal rod that is adjustable relative to the first bore hole to adjust the position and/or orientation of the second spinal rod relative to the first spinal rod. The rod connector may comprise a first housing component defining the first bore hole and a second housing component that is movable relative to the first housing component and defining the second bore hole.

21 Claims, 6 Drawing Sheets

Related U.S. Application Data continuation of application No. 13/540,770, filed on Jul. 3, 2012, now Pat. No. 8,852,237, which is a continuation of application No. 10/815,883, filed on Mar. 31, 2004, now Pat. No. 8,236,028.

(58) Field of Classification Search
USPC ........ 606/246, 250–253, 259, 260, 264–266, 606/270, 277, 278, 279; 411/393; 403/286, 362
See application file for complete search history.

(56) References Cited

U.S. PATENT DOCUMENTS

| | | | |
|---|---|---|---|
| 5,053,034 A | 10/1991 | Olerud | |
| 5,474,551 A | 12/1995 | Finn et al. | |
| 5,582,612 A | 12/1996 | Lin | |
| 5,630,816 A | 5/1997 | Kambin | |
| 5,643,263 A | 7/1997 | Simonson | |
| 5,658,284 A | 8/1997 | Sebastian et al. | |
| 5,669,910 A * | 9/1997 | Korhonen | A61B 17/7052 606/151 |
| 5,910,142 A | 6/1999 | Tatar | |
| 5,947,967 A | 9/1999 | Barker | |
| 5,976,135 A | 11/1999 | Sherman et al. | |
| 5,980,521 A | 11/1999 | Montague et al. | |
| 6,231,575 B1 * | 5/2001 | Krag | A61B 17/7041 606/264 |
| 6,264,658 B1 | 7/2001 | Lee et al. | |
| 6,283,658 B1 | 9/2001 | Estevez et al. | |
| 6,283,967 B1 | 9/2001 | Troxell et al. | |
| 6,520,962 B1 | 2/2003 | Taylor et al. | |
| 6,524,310 B1 | 2/2003 | Lombardo et al. | |
| 6,562,038 B1 | 5/2003 | Morrison | |
| 6,579,292 B2 | 6/2003 | Taylor | |
| 6,620,164 B2 | 9/2003 | Ueyama et al. | |
| 6,626,906 B1 | 9/2003 | Young | |
| 6,676,661 B1 | 1/2004 | Martin Benlloch et al. | |
| 6,685,705 B1 | 2/2004 | Taylor | |
| 6,716,213 B2 | 4/2004 | Shitoto | |
| 9,011,496 B2 * | 4/2015 | Harper | A61B 17/7038 606/250 |
| 2002/0138077 A1 | 9/2002 | Ferree | |
| 2002/0143327 A1 | 10/2002 | Shluzas | |
| 2003/0032959 A1 | 2/2003 | Yeh | |
| 2003/0153914 A1 | 8/2003 | Oribe et al. | |
| 2003/0153917 A1 | 8/2003 | Richelsoph et al. | |
| 2004/0039385 A1 | 2/2004 | Mazda et al. | |
| 2004/0116928 A1 | 6/2004 | Young et al. | |
| 2005/0131404 A1 | 6/2005 | Mazda et al. | |
| 2005/0154388 A1 | 7/2005 | Roussouly et al. | |
| 2005/0171538 A1 | 8/2005 | Sgier et al. | |

FOREIGN PATENT DOCUMENTS

| | | |
|---|---|---|
| EP | 1312316 A3 | 8/2003 |
| FR | 2781359 A1 | 7/1998 |
| WO | WO 2001001872 A1 | 1/2001 |
| WO | WO 2002034151 A2 | 5/2002 |
| WO | WO 2002034151 A3 | 7/2002 |

OTHER PUBLICATIONS

European Office Action for Application No. 09178430.6, 6 pages, dated Dec. 20, 2010.

European Office Action for Application No. 10190633.7, 6 pages, dated Dec. 17, 2012.

European Office Action for Application No. 09178430.6, 7 pages, dated Nov. 18, 2013.

* cited by examiner

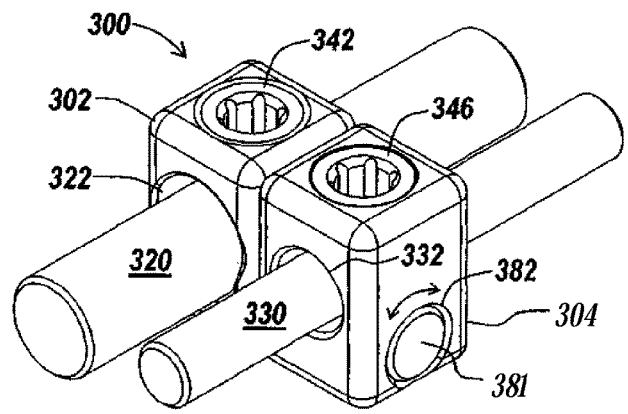
*Fig. 4A*
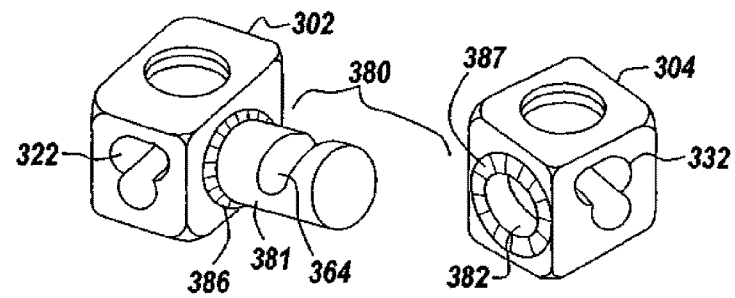
*Fig.4B*
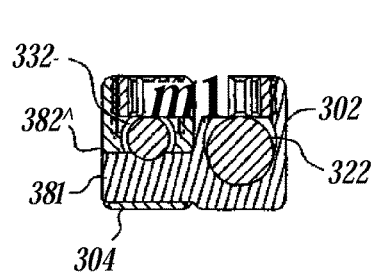
*Fig.4C*
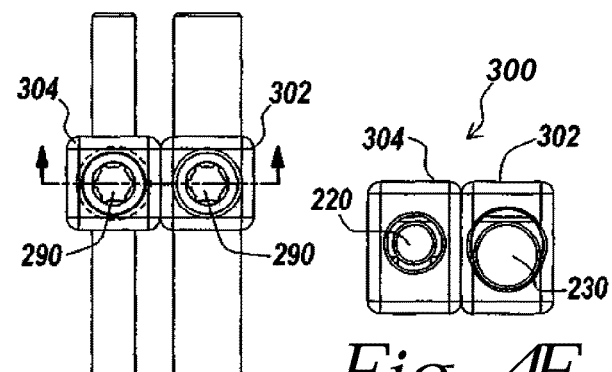
*Fig. 4D*   *Fig. 4E*

SPINAL ROD CONNECTOR

CROSS REFERENCE TO RELATED APPLICATIONS

This application is a continuation application of U.S. patent Continuation application Ser. No. 14/334,994, filed Jul. 18, 2014, entitled "SPINAL ROD CONNECTOR", which claims priority to U.S. Patent Continuation application Ser. No. 13/540,770, filed Jul. 3, 2012, entitled "SPINAL ROD CONNECTOR" (Now U.S. Pat. No. 8,852,237), which claims priority to U.S. Non-Provisional application Ser. No. 10/815,883, filed Mar. 31, 2004, entitled "SPINAL ROD CONNECTOR", (Now U.S. Pat. No. 8,236,028), all applications are herein incorporated by reference in their entireties.

FIELD OF THE INVENTION

The present invention relates to a spinal fixation systems used to retain positions of a spinal column, such as vertebrae, in a desired spatial relationship. More particularly, the present invention relates to a component of a spinal fixation system for connecting a first rod to a second rod.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae.

The length of the cylindrical rod depends on the size and number of vertebrae to be held in a desired spatial relationship relative to each other by the apparatus. The rods may be bent, as desired, to conform to a desired curvature of the spinal column in one or more of the anatomic planes. The size of the spinal rod depends on the region of the spine where the spinal fixation system is used. For example, in the cervical region of the spine, where the vertebrae tend to be smaller, a relatively smaller spinal rod is used, which is positioned close to the center of the spine. In the thoracic region, where heavier loads are experienced and the vertebrae tend to be larger, a rod having a larger diameter is used. The cervico-thoracic junction of the spine is typically fused using rods of two different diameters to accommodate anatomical differences between the cervical and thoracic spine regions. To accommodate a system including spinal rods having different sizes and configurations, a rod connector may be used to join a first rod and a second rod. The rod connector may be a side-by-side connector, where the ends of the two rods are placed side-by-side and connected using a connector that spans the two ends, or an axial connector, which aligns the axes of the two rods and connects the ends of the rods together along the axial direction.

Prior rod-to-rod connectors for the cervico-thoracic junction are static and include fixed, parallel bore holes for receiving spinal rods that are spaced an equal distance from the spinal column, i.e., having axes that are aligned in the sagittal plane of the patient when the connector is implanted. However, the spinal support rods that are joined using a rod connector are frequently oriented at various angles and positions due to the anatomical structure of the patient, the physiological problem being treated, and the preference of the physician. Because the two rods are configured to accommodate variations in the spinal column, the portions of the rods that are connected by the connector may not be parallel to each other, or spaced the same distance from the spinal column. The discrepancy must be fixed by bending the rods in other regions, such that the portions that insert in the bore holes are aligned and parallel with each other. However, bending tends to weaken the rods and can be an imprecise method for ensuring that the rods fit in the connector.

SUMMARY OF THE INVENTION

The present invention provides an improved rod connector in a spinal fixation system for connecting a first spinal rod to a second spinal rod. The rod connector provides an offset or non-parallel connection between the rods that allows the rods to match the contour of a patient's spinal column without requiring bending of the rods. The rod connector may include a first bore hole for receiving the first spinal rod and a second bore hole for receiving the second spinal rod that is adjustable relative to the first bore hole to adjust the position and/or orientation of the second spinal rod relative to the first spinal rod. The rod connector may comprise a first housing component defining the first bore hole and a second housing component that is movable relative to the first housing component and defining the second bore hole. The second bore hole may be made adjustable using a spherical bushing to allow a spinal rod received in the second bore hole to pivot within the bore hole to adjust the position of the spinal rod relative to the first spinal rod.

According to a first aspect of the invention, a connector for connecting a first rod and a second rod comprises a housing component and a locking element. The housing component defines a first bore hole for receiving a portion of the first rod and a second bore hole for receiving a portion of the second rod. The first bore hole extends along a first longitudinal axis and the second bore hole extends along a second longitudinal axis. The locking element secures one of the first rod within the first bore hole and the second rod within the second bore hole. The first longitudinal axis is offset from the second longitudinal axis by a predetermined offset distance.

According to another aspect of the invention, a connector for connecting a first rod and a second rod comprises a housing component and a locking element. The housing component defines a first bore hole for receiving a portion of the first rod and a second bore hole for receiving a portion of the second rod. The first bore hole extends along a first longitudinal axis and the second bore hole extends along a second longitudinal axis that is non-parallel with the first longitudinal axis. The locking element secures one of the first rod within the first bore hole and the second rod within the second bore hole.

According to another aspect of the invention, a connector for connecting a first rod and a second rod comprises a first housing component defining a first bore hole for receiving a portion of the first rod and a second housing component coupled to the first housing component. The second housing component defines a second bore hole that is movable relative to the first bore hole for receiving a portion of the second rod.

According to another aspect of the invention, a method of connecting a first rod to a second rod, comprises the steps of inserting the first rod into a first bore hole of a rod connector, inserting the second rod into a second bore hole of the rod connector and moving the second bore hole relative to the first bore hole.

According to still another aspect, a connector for connecting a first rod and a second rod comprises a housing component, which defines a first bore hole for receiving a portion of the first rod and a second bore hole for receiving a portion of the second rod, and a locking element for securing one of the first rod within the first bore hole and the second rod within the second bore hole. A first longitudinal axis of the first bore hole is configured to be offset from a second longitudinal axis of the second bore hole in a first plane by a first predetermined offset distance and by a second predetermined offset distance in a second plane that is perpendicular to the first plane.

According to another aspect, connector for connecting a first rod and a second rod is provided, which comprises a housing component having a top surface, a bottom surface, a front surface and a back surface and a locking element inserted through the top surface for securing one of the first rod within a first bore hole defined by the housing component and the second rod within a second bore hole defined by the housing component. The first bore hole is offset from the second bore hole, such that said first bore hole is closer to the bottom surface of the housing than the second bore hole

BRIEF DESCRIPTION OF THE DRAWINGS

FIGS. 4A-4E illustrate different views of a rod connector comprising first and second housing components including a coupling rod for rotatably coupling the first housing component to the second housing component.

DETAILED DESCRIPTION OF THE INVENTION

The present invention provides an improved rod connector for connecting a first rod and a second rod in a region of the spine, such as the cervico-thoracic junction region of the spine. The rod connector of the present invention reduces or eliminates the need for bending connected rods. The invention will be described relative to illustrative embodiments, though one skilled in the art will recognize that the invention is not limited to the described embodiments. While the rod connector is used primarily in the cervico-thoracic junction region of the spine, the rod connector may also be employed to couple any type of component used in an orthopedic implant system.

Figure 1:
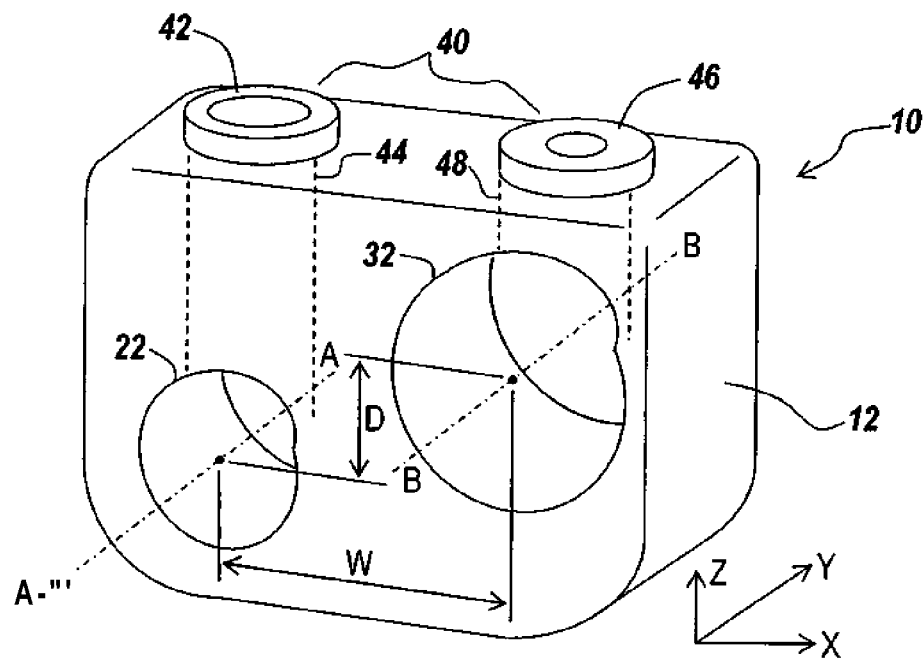
FIG. 1 illustrates a rod connector including off-set bore holes for receiving rods according to an embodiment of the invention.

FIG. 1 illustrates a rod connector 10 for connecting a first spinal rod, such as a cervical rod, and a second spinal rod, such as a thoracic rod, in a cervico-thoracic junction region of the spine according to an embodiment of the present invention. The rod connector 10 may be used in an occipito-cervico-thoracic spinal fixation system for rigid posterior fixation of the occipito-cervico-thoracic regions of the spine, though the rod connector may alternatively be used in any suitable location to connect any suitable components of an orthopedic system.

The rod connector 10 includes a housing 12 defining a first bore hole 22 for receiving a portion of the first rod and a second bore hole 32 for receiving a portion of the second rod. Preferably, the rod connector 10 receives the end portions of each rod, though one skilled in the art will recognize that the rod connector can connect any suitable portion of a rod. The housing may be formed of any suitable bio-compatible material, including, but not limited to stainless steel, titanium, plastic, and mixtures thereof.

According to the illustrated embodiment, each bore hole 22, 32 is formed by a pair of circular openings having centers which are offset along a central axis, such that each bore hole has a generally oval cross-sectional configuration. The size of the circular openings which cooperate to form the rod bore holes are such that the associated rod can move between the upper and lower portion of the bore hole. The lower circular opening is preferably slightly smaller in diameter than the associated rod, to provide an interference fit between the housing and the rod when the rod is inserted in the lower circular opening. For example, the first bore hole 22 may be configured to receive a cervical rod, which has a diameter of less than about 4 millimeters and preferably between about 2.5 millimeters and about 3.5 millimeters. The second bore hole 32 may be configured to receive a thoracic rod, which has a diameter of between about 4.75 millimeters and about 6.35 millimeters and preferably about 3.5 millimeters.

One skilled in the art will recognize that the shape and size of the bore holes is not limited to the illustrated embodiment, and that the bore hole may have any suitable size and/or shape for receiving a rod. For example, the bore holes may alternatively have a circular or polygonal cross-section.

The rod connector 10 further includes a locking mechanism 40 for securing one or both of the rods to the housing 12. In the illustrated embodiment, the locking mechanism 40 comprises a first set screw 42 disposed in a first screw passage 44 that extends traverse to and intersects with the first bore hole 22 and a second set screw 46 disposed in a second screw passage 48 that extends traverse to and intersects with second bore hole 32. To secure each rod to the rod connector 10, the each set screw is tightened in the associated set screw passage after the rod is inserted in the bore hole. As the set screw is tightened, force is transmitted from the set screw to the rod to secure the rod within the bore hole.

In the embodiment shown in FIG. 1, the first bore hole 22 has a first central longitudinal axis -A-A- along which the first bore hole 22 extends and the second bore hole has a second central longitudinal central axis -B-B- along which the second bore hole 32 extends. The bore holes 22, 32 are offset from each other, such that when the rod connector 10 is inserted in a patient, the -B-B- axis of the second bore hole 32 is offset from the -A-A- axis of the first bore hole 22 in the sagittal plane, i.e., the longitudinal plane that divides the body of a bilaterally symmetrical animal into right and left sections. (The sagittal plane is parallel to the YZ axis shown in FIG. 1). The offset of the bore holes in the sagittal plane positions one of the bore holes, illustrated as the second bore hole 32, closer to the spine and the bottom surface of the connector than the other bore hole. As shown, the axis -B-B- of the second bore hole is offset from the axis -A-A- of the first bore hole by a first predetermined distance W in a first plane, and by a second predetermined distance D in a second plane, which aligns with the sagittal plane, that is perpendicular to the first plane. As shown, the first plane is parallel to the XY plane and the second plane is parallel to the YZ plane.

The rod connector 10 of FIG. 1 contrasts conventional spinal rod connectors, in which the longitudinal axes of the bore holes are aligned in the sagittal plane, i.e., the same vertical distance from the spine. By offsetting the longitudinal axes of the bore holes in a vertical direction, the ends of the first and second rods can be placed varying distances from the spine without requiring the surgeon to bend one or more of the rods to accommodate a particular spinal configuration. The longitudinal axis -A-A- may be parallel to the offset axis -B-B-, or the axes may be skewed relative to each other. The offset distance D may be any suitable distance depending on a particular application. In the embodiment of FIG. 1, the first bore hole 22 is placed closer to the spine than the second bore hole 32 by the distance D, though one skilled in the art will recognize that the second bore hole 32 may alternatively be positioned closer to the spine than the first bore hole.

According to one aspect, a surgeon can select an appropriate rod connector having a suitable offset distance from a selection of rod connectors having different offset distances, based on a particular spinal configuration.

Figure 2:
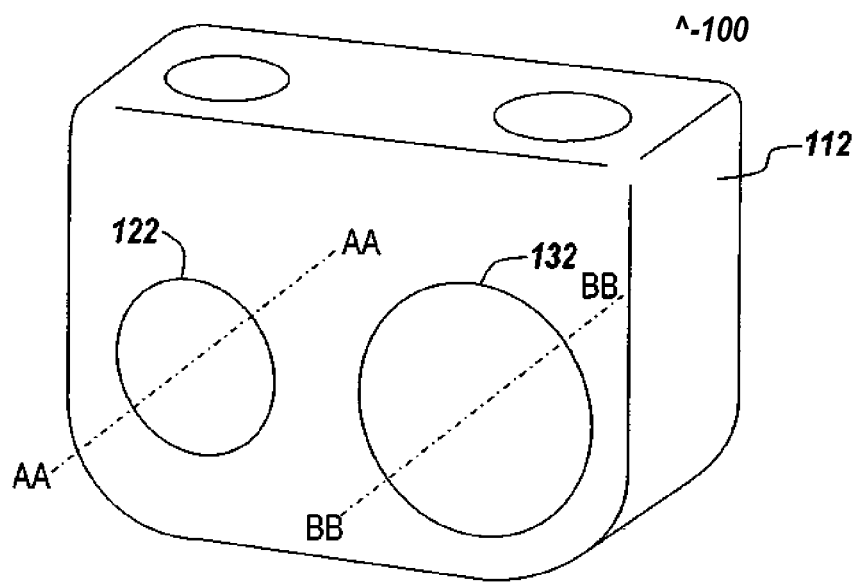
FIG. 2 illustrates a rod connector including non-parallel bore holes for receiving rods according to another embodiment of the invention.

According to another embodiment of the invention, shown in FIG. 2, a rod connector 100 may include bore holes that extend along longitudinal axes that are non-parallel, such that the portions of the rods seated within the connector are non-parallel to each other. The rod connector 100 includes a housing 112 defining a first bore hole 122 extending along a first longitudinal axis -AA-AA- for receiving a first spinal rod and a second bore hole 132 extending along a second longitudinal axis -BB-BB- for receiving a second spinal rod.

The second longitudinal axis is skewed relative to the first longitudinal axis to allow the rods to extend in a non-parallel direction. The longitudinal axis of each bore hole may extend at any suitable angle to accommodate a particular spinal configuration. For example, the first bore hole 122 can extend in a direction that is parallel to the longitudinal axis of the spine, while the second bore hole is angled relative to the longitudinal axis of the spine and the first bore hole. Alternatively, both bore holes may be skewed relative to the axis of the spine. One skilled in the art will recognize that the first and second bore holes may extend at any suitable angle relative to the longitudinal axis and/or each other, depending on the particular curvature of the spinal column. In addition, the first longitudinal axis -AA-AA- and the second longitudinal axis -BB-BB- may be aligned relative to the spine or offset, as shown in FIG. 1.

Figure 3:
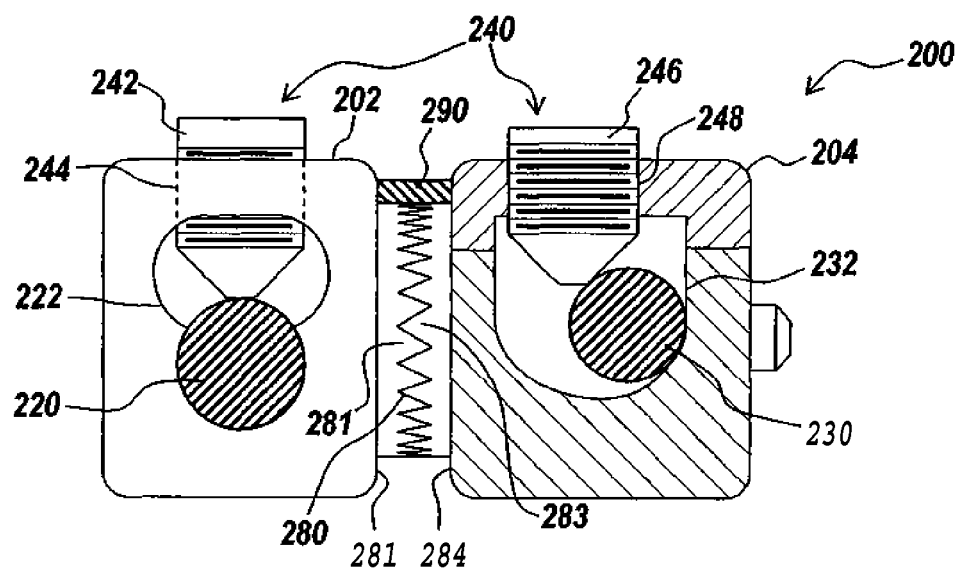
FIG. 3 illustrates a rod connector comprising adjustable housing components defining bore holes for receiving rods according to another embodiment of the invention.

According to one aspect, a surgeon can select an appropriate rod connector having suitable bore hole angles from a selection of rod connectors having bore holes extending at a variety of different angles, based on a particular spinal configuration FIG. 3 illustrates a rod connector 200 comprising a plurality of housing components that are movable with respect to each other to adjust the position, angle or orientation of the rods relative to each other, according to another embodiment of the invention. The rod connector 200 allows a surgeon to modify the connector to accommodate a particular junction region, without permanently altering the connector and/or the rods. The rod connector 200 comprises a first housing component 202 including a first bore hole 222 for receiving a first rod 220 and a second housing component 204 coupled to the first housing component 202 and including a second bore hole 232 for receiving a second rod 230.

A locking mechanism 240 is also provided for securing one or both of the rods to the housing. In FIG. 3, the locking mechanism 240 comprises a first set screw 242 disposed in a first set screw passage 244 for securing the first rod 220 and a second set screw 246 disposed in a second set screw passage 248 for securing the second rod 230.

The rod connector 200 further includes a coupling mechanism 280 for movably coupling the first housing component 202 to the second housing component 204 to thereby connect the first rod and the second rod. In the embodiment shown in FIG. 3, the coupling mechanism 280 comprises a first set of external teeth 281 on an outside surface 282 of the first housing component 202 and a second set of external teeth 283 on an outside surface 284 of the second housing component that faces the outside surface 282 of the first housing component. The first and second sets of external teeth mesh to set the position of first housing component and second housing component in a vertical direction.

A clamping mechanism 290 may also be provided for clamping the two housing components 202, 204 together after the coupling mechanism 280 places the first and second housing components into a selected position relative to each other. The clamping mechanism 290 may comprise any suitable means for securing the second housing component 204 relative to the first housing component 202, including, but not limited to one or more screws, adhesive and a crimping tool.

The coupling mechanism 280 may enable relative movement of the first housing component relative to the second housing in one or more suitable directions. For example, in the embodiment shown in FIG. 3, the coupling mechanism 280 comprises interlocking teeth connect at discrete locations to vary the offset distance D of the central longitudinal axis of the first and second bore holes, thereby varying the elevation of one or more of the rods relative to the spine. However, the coupling mechanism 280 may alternatively allow the first housing component to rotate relative to each other to vary the angle between the bore holes, or vary the lateral distance between the housing components to vary the distance between the bore holes. One skilled in the art will recognize that any suitable means may be used to alter the orientation of the first bore hole relative to the second bore hole in the rod connector 200 of FIG. 3.

The use of adjustable housing components in a rod connector allows a user to adjust the relative position and/or orientation of the connected spinal rods without replacing or damaging the rod connector. The relative position and/or orientation of the bore holes can be adjusted before the spinal rods are inserted in the rod connector, after one of the spinal rods is inserted in the rod connector, or after both of the spinal rods have been inserted in the rod connector. For example, according to one embodiment, a surgeon may select an initial orientation of the bore holes by selectively positioning the housing components relative to each other. After implantation of the spinal fixation system, the surgeon may readjust the rod connector housing components to vary the relative position of the bore holes to accommodate changes in the contour of the spine over time.

As shown in FIGS. 4A-E, a coupling mechanism 380 for a rod connector of the present invention can alternatively comprise a protrusion extending from one of the housing components and a recess on the other housing component configured to receive the protrusion. For example, in the rod connector 300 shown in FIGS. 4A-E, a transversely extending coupling rod 381 on one of the housing components, illustrated as the first housing component 302, cooperates with a coupling opening 382 on the other housing component, illustrated as the second housing component 304. The coupling opening 382 is sized and dimensioned to receive the coupling rod 381.

The coupling mechanism 380 allows the first housing component 302 to move both laterally and angularly relative to the second housing component 304 before and/or after implantation of the rod connector in a patient. For example, the lateral distance between the bore holes 322, 332, and thus the rods joined by the connector 300 can be adjusted by adjusting the depth of insertion of the coupling rod 381 within the coupling opening 382 to control the distance between the two housing components. The angular position of the bore holes 322, 332, relative to each other can be adjusted by rotating the first housing component about coupling rod pivot the first housing component 302 relative to the second housing component 304. In the illustrative embodiment, the coupling rod 381 has a circular cross section to allow infinite rotation in the sagittal plane, while facilitating medial/lateral adjustment between the rods.

The rod connector of the present invention may further includes a rod seat in one or both of the housing components for seating a rod in the bore hole of the housing component.

In the embodiment shown in FIGS. 4A-E, the rod seat comprises a lateral groove 364 on the coupling rod 381 for directly seating the spinal rod 330 thereon.

As shown in FIG. 4B, the housing components 302, 304 may further include optional external teeth 381, 383, respectively, to facilitate coupling of the housing components. The teeth 386, 387 provide discrete positions for the housing components relative to each other, while increasing the coupling strength between the housing components.

Figure 5:
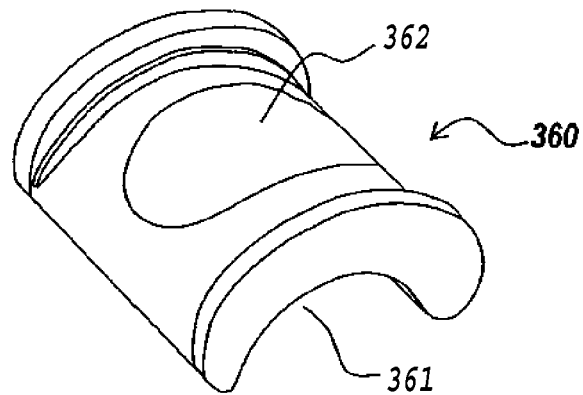
FIG. 5 illustrates an embodiment of a compression chip for use with a rod connector having a coupling rod.

Alternatively, the rod seat may comprise a compression chip 360, shown in FIG. 5, disposed between the rod 330 of the second housing component and the coupling rod 381 of the first housing component 302 when the rod connector 300 is assembled. The compression chip 360 of the illustrated embodiment comprises an arc-shaped component forming a bottom channel 361 that is complementary to the coupling rod 381 and having a top groove 362 that is complementary to the bottom of the associated rod 330. Advantages of using a compression chip, such as the compression chip 360 shown in FIG. 5, include a greater surface area contact between the rod 330 of the second housing component and the coupling rod 381, which provides a more stable connection between the housing components. The compression chip 360 also facilitates media-lateral translation between the housing components to vary the distance between the rods in a media-lateral plane.

The spinal rod may alternatively be directly seated on the inserted coupler rod through point-on-point contact when the rod connector is assembled. One skilled in the art will recognize that the rod seat may have any suitable configuration and location for seating a spinal rod.

After the housing components are positioned relative to each other using the coupling mechanism 380, a clamping mechanism secures the position of the first housing component 302 relative to the second housing component 304. In the embodiment shown in FIGS. 4A-E, the clamping mechanism for securing the housing components is also a locking mechanism for securing the spinal rods in the respective bore holes. After assembly and positioning of the housing components 302, 304 relative to each other in a selected position and insertion of the spinal rods 320, 330 in the respective bore holes 322, 332, respectively, a first set screw 342 is inserted in a first screw passage 344 and a second set screw is 346 inserted in a second screw passage 348. The second set screw 346 is tightened to compress the second spinal rod 330, the rod seat and the coupling rod 381 together to secure the position of the coupling rod within the coupling passage and lock the spinal rod 330 within the bore hole 332. The first set screw 342 is also tightened to secure the first spinal rod 320 in the first bore hole 322.

In the embodiment of FIGS. 4A-E, the coupling opening 382 extends through the second housing component 304 and the coupling rod 381 extends through the second housing component 304 when the two housing components are positioned adjacent to each other. However, one skilled in the art will recognize that the coupling opening 382 and coupling rod may have any suitable size, length and configuration for coupling the first housing component to the second housing component in a selected position and orientation.

While the embodiment of FIGS. 4A-E illustrates the coupling rod 381 as a protrusion extending from the first housing component 302 below and transverse to the first bore hole 322 and the coupling hole 382 as a passageway extending below and transverse to the second bore hole 332 in the second housing component 304, one skilled in the art will recognize that the invention is not limited to the illustrated configuration. For example, the coupling rod may alternatively be provided on the second housing component and the corresponding coupling hole may be provided on the first housing component. The coupling rod and coupling hole may also be provided above or below the corresponding bore hole.

Figure 6A:
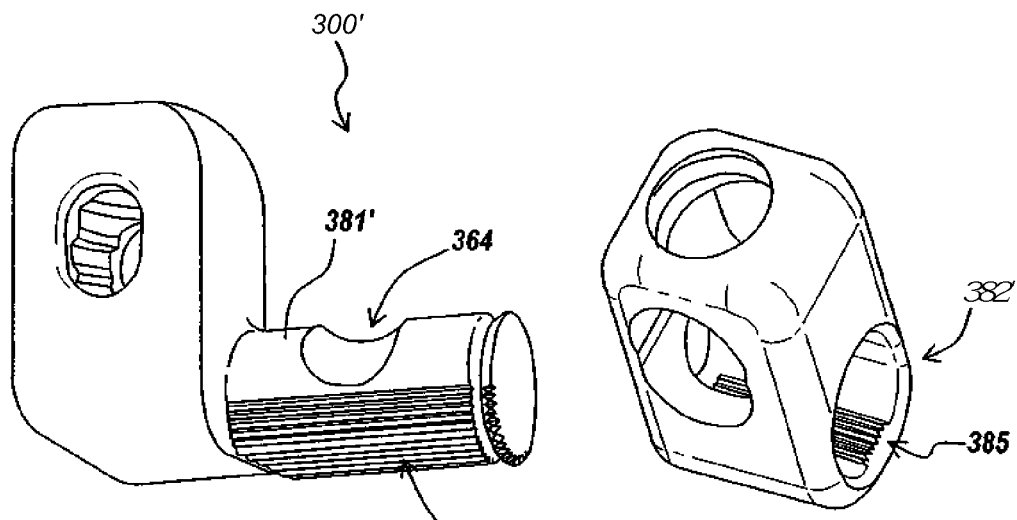
FIGS. 6A-C illustrates different views of an alternative embodiment of the rod connector of FIGS. 4A-4E, wherein the coupling rod includes interlocking teeth.
Figure 6B:
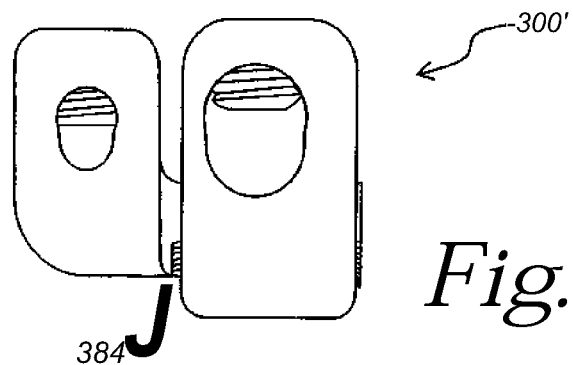
Figure 6C:
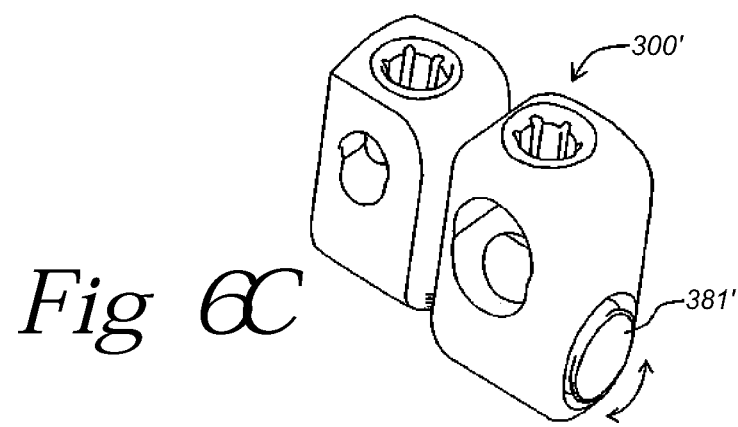

As shown in FIGS. 6A-6C, a rod connector 300' may include a coupling rod 381' having external teeth 384 configured to cooperate with teeth 385 on the coupling opening 382'. The use of interlocking teeth increased the coupling strength between the housing components, while providing discrete rotation positions between the housing components.

Figure 7:
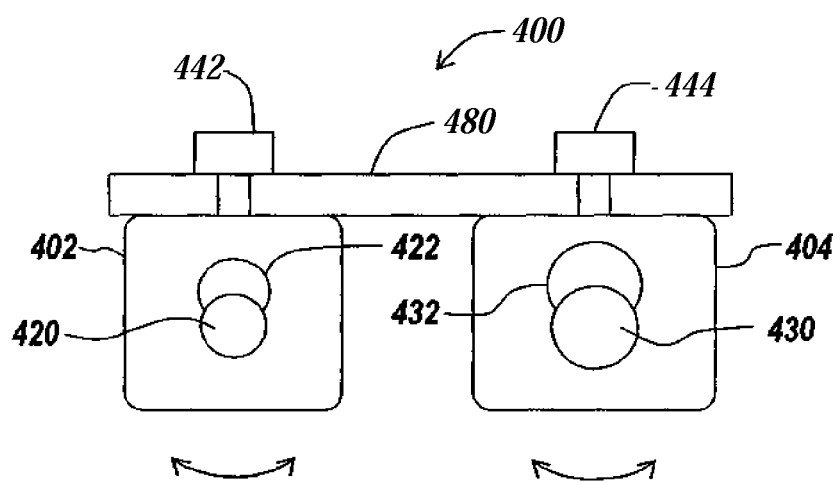
FIG. 7 illustrates a rod connector including pivotably mounted housing components.
Figure 8A:
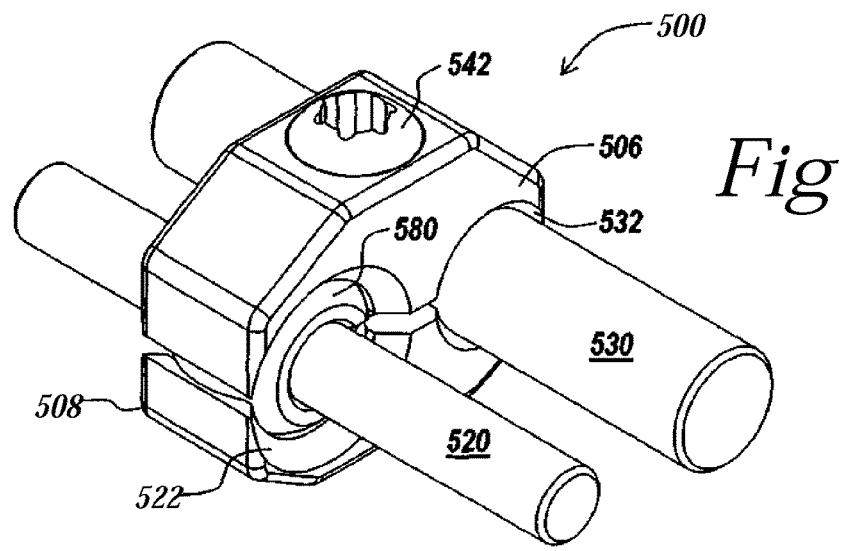
FIGS. 8A-8D illustrates different views of a rod connector including a spherical bushing in a bore hole for adjusting a longitudinal axis of the bore hole.
Figure 8B:
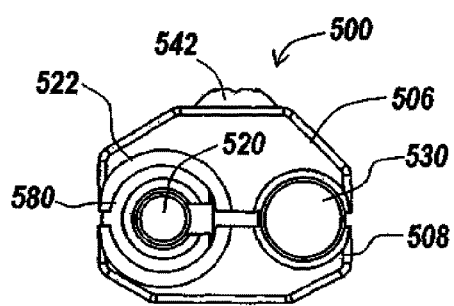
Figure 8D:
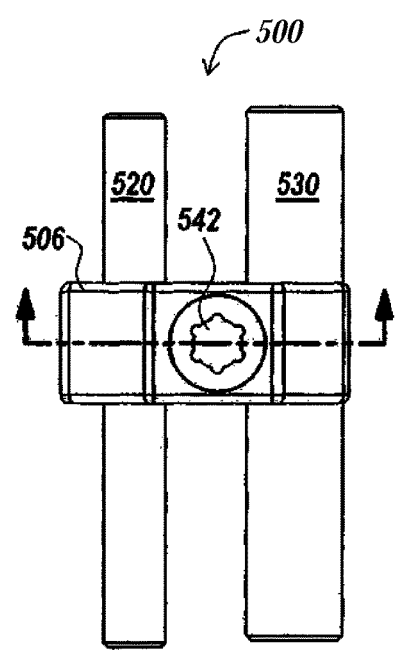
Figure 8C:
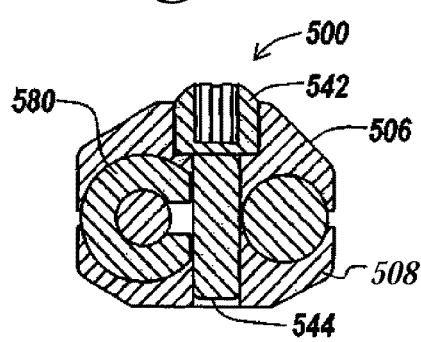

According to yet another embodiment of the invention, as shown in FIG. 7, a rod connector 400 for coupling a first rod 420 to a second rod 430 may comprise a plurality of housing components 402, 404 that are pivotably mounted to a connecting component 480. The first housing component 402 includes a first bore hole 422 for receiving the first rod 420 and the second housing component 404 includes a second bore hole for receiving the second rod 430. One or both of the housing component 402, 404 is rotatably mounted to a transversely extending connecting component 480 using screws 442, 444 or other suitable means. The relative position of the housing components is adjusted by rotating each housing component about the axis of the screws 442, 444 to vary the angle of each bore hole 422, 432 relative to each other and the longitudinal axis of the spine. After pivoting each housing component into a selected position, the screws 442, 444 are tightened to lock the position of each housing component 402, 404, respectively, thereby creating a rigid rod connector for fixing the position of the first rod 420 and the second rod 430 relative to each other.

According to another embodiment of the invention, as shown in FIGS. 8A-8D, a rod connecter 500 may include a spherical bushing in one or more of the bore holes for receiving a spinal rod to allow the corresponding spinal rod to move relative to the housing of the rod connector. For example, in the embodiment shown in FIGS. 8A-8D, the rod connector 500 comprises a top housing component 506 defining a top half of a first bore hole and a top half of a second bore hole. The rod connector 500 also includes a bottom housing component 508 defining a bottom half of the first bore hole and a bottom half of the second bore. The top housing component 506 and bottom housing component cooperate to defining a first bore hole 522 for receiving a first spinal rod 520 and a second bore hole 532 for receiving a second spinal rod 530 when assembled together. A spherical bushing 580 is providing in one of the bore holes, illustrated as the first bore hole 522, around the associated spinal rod 520 for allowing the spinal rod to move relative to the housing 506. The bushing 580 thus allows for the position of the first spinal rod to be adjusted relative to the position of the second spinal rod without bending or modifying the rods.

After moving the first spinal rod 520 into a selected position relative to the housing 506 and second spinal rod 530, the housing components are fixed using a locking mechanism, illustrated as a top-loading set screw 542 disposed in a screw passage 544 extending between the top housing 506 component and the bottom housing component 508. The screw 542, when tightened, locks the housing components together, fixing the spinal rods 520, 530, within the bore holes 522, 532, respectively, and fixing the position of the first spinal rod 520, as defined by the orientation of the spherical bushing 580, relative to the second spinal rod 530.

According to an alternate embodiment, a locking mechanism for securing the position of the spinal rods within the rod connector may comprise a plurality of screws. For example, the locking mechanism may comprise a first screw and a second screw disposed on the outside of the bore holes for locking the housing components together and fixing the relative positions of the spinal rods.

The housing of the rod connector 500 is also not limited to a top and bottom housing component and may alternatively comprise a unitary housing component defining the first and second bore holes, or other suitable configuration.

While the invention has been described relative to a side-by-side rod connector, one skilled in the art will recognize that the principles and concepts of the invention also apply to an axial connector having bore holes arranged on opposite ends of the connector and facing different directions. Examples of such end-to-end connectors are described in commonly owned U.S. Ser. No. 10/708,919 (U.S. Pat. No. 7,909,852), entitled "Adjustable-Angle Spinal Fixation Element", the contents of which are herein incorporated by reference.

The rod connector of the present invention provides significant advantages over prior rod connectors for connecting two spinal rods. The rod connector accommodates variations in the contour of the spine in different regions without bending and subsequent weakening of the spinal rod. The rod connector allows a surgeon to precisely select and adjust, if necessary, the angle and/or distance between the two bore holes receiving the spinal rods. In this manner, the rod connector facilitates alignment, adjustment and/or fixation of the vertebrae in a desired spatial relationship relative to each other.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

We claim:

1. A spinal connector for connecting a first rod and a second rod, comprising:
   a housing defining a first bore hole for receiving a portion of the first rod, the first bore hole extending along a first longitudinal axis and a second bore hole for receiving a portion of the second rod, the second bore hole extending along a second longitudinal axis, wherein the first longitudinal axis and the second longitudinal axis are generally parallel;
   a set screw for securing at least one of the first rod within the first bore hole and the second rod within the second bore hole;
   a rod seat component disposed in the housing for seating at least one of the first rod in the first bore hole and the second rod in the second bore hole, wherein the rod seat component comprises a top surface and a bottom surface generally opposite the top surface, the top surface includes a groove that is sized and configured to receive at least a portion of one of the first rod and the second rod, and wherein the groove defines a minor arc.

2. The spinal connector of claim 1 wherein the rod seat component comprises a compression clip.

3. The spinal connector of claim 2 wherein the compression clip is disposed between at least a portion of the housing and at least one of the first rod and the second rod.

4. The spinal connector of claim 2, wherein the compression clip is an arc-shaped component.

5. The spinal connector of claim 1, wherein the housing comprises a first housing component defining the first bore hole and a second housing component movably coupled to the first housing component and defining the second bore hole, the first housing component comprising a coupling rod extending in a direction that is transverse to the first longitudinal axis and the second housing component including a coupling hole configured to receive the coupling rod.

6. The spinal connector of claim 5, wherein the rod seat component comprises a compression clip disposed in the second housing component.

7. The spinal connector of claim 5, wherein the compression clip is an arc-shaped component.

8. The spinal connector of claim 7, wherein the compression clip forms a channel that is sized and configured to receive at least a portion the coupling rod.

9. The spinal connector of claim 8, wherein the compression clip is disposed between the coupling rod and at least one of the first rod and the second rod.

10. The spinal connector of claim 5, wherein the first longitudinal axis is configured to be offset in a sagittal plane from the second longitudinal axis by a predetermined offset distance when the spinal connector is implanted in a patient.

11. The spinal connector of claim 10, wherein the first longitudinal axis is configured to be offset in a sagittal plane from the second longitudinal axis by a variable offset distance when the spinal connector is implanted in a patient.

12. The spinal connector of claim 5, wherein the first housing component includes a first set of external teeth on an outer surface thereof and the second housing component includes a second set of external teeth on an outer surface thereof.

13. The spinal connector of claim 12, wherein the first set of external teeth and the second set of external teeth are configured to interlock at a plurality of discrete positions.

14. The spinal connector of claim 5, wherein the coupling rod includes a first set of teeth on an outside surface and the coupling hole includes a second set of teeth on an inside surface configured to contact the first set of teeth of the coupling rod.

15. The spinal connector of claim 5, further comprising a clamping mechanism configured to secure the first housing component in a selected position relative to the second housing component.

16. The spinal connector of claim 5, wherein the first bore hole is formed by a pair of opening holes extending along the first longitudinal axis and having centers which are offset along a central axis.

17. The spinal connector of claim 16, wherein one of the opening holes is sized to provide an interference fit between the first housing component and the first spinal rod.

18. The spinal connector of claim 5, wherein the second bore hole is formed by a pair of opening holes extending along the second longitudinal axis and having centers which are offset along a central axis.

19. The spinal connector of claim 18, wherein one of the opening holes is sized to provide an interference fit between the second housing component and the second spinal rod.

20. The spinal connector of claim 1 wherein the minor arc is less than 180 degrees.

21. The spinal connector of claim 1 wherein the bottom surface includes a concavity.

* * * * *